US010785997B2

(12) United States Patent
Kim et al.

(10) Patent No.: US 10,785,997 B2
(45) Date of Patent: Sep. 29, 2020

(54) STERILIZER HAVING REINFORCEMENT RIB

(71) Applicant: CJ Cheiljedang Corporation, Seoul (KR)

(72) Inventors: Jong Chul Kim, Busan (KR); Sung Mo Geum, Busan (KR); Hak Bae Kim, Busan (KR); Jun Mo Gu, Busan (KR); Gun Dong Kim, Busan (KR); Myung Ho Kim, Busan (KR); Han Seul Lee, Busan (KR); Eun Hye Kim, Pyeongtaek-si (KR); Hye Mi Choi, Gumi-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 116 days.

(21) Appl. No.: 15/746,372

(22) PCT Filed: Jul. 21, 2016

(86) PCT No.: PCT/KR2016/007938
§ 371 (c)(1),
(2) Date: Jan. 19, 2018

(87) PCT Pub. No.: WO2017/014571
PCT Pub. Date: Jan. 26, 2017

(65) Prior Publication Data
US 2018/0192674 A1  Jul. 12, 2018

(30) Foreign Application Priority Data
Jul. 21, 2015  (KR) .................. 10-2015-0102990

(51) Int. Cl.
*A61L 2/07* (2006.01)
*A23L 3/04* (2006.01)
(Continued)

(52) U.S. Cl.
CPC ............... *A23L 3/04* (2013.01); *A23B 9/025* (2013.01); *A23L 3/001* (2013.01); *A23L 3/10* (2013.01);
(Continued)

(58) Field of Classification Search
CPC ........................................... A61L 2/07
See application file for complete search history.

(56) References Cited

U.S. PATENT DOCUMENTS 1,681,101 A * 8/1928 Coyle .................. A23L 3/001
198/775
2,017,399 A * 10/1935 Galvin .................. A23L 3/04
99/366
(Continued)

FOREIGN PATENT DOCUMENTS

CN      1180499 A    5/1998
CN    101125210 A    2/2008
(Continued)

OTHER PUBLICATIONS

Matsumoto KR 101231997. Feb. 8, 2013. English machine translation. (Year: 2013).*

*Primary Examiner* — Donald R Spamer
(74) *Attorney, Agent, or Firm* — Seed Intellectual Property Law Group LLP (57) ABSTRACT

The present invention provides a sterilizer which includes a steam chamber comprising a steam chamber upper member and a steam chamber lower member which are bolt-coupled to each other; an inlet door configured to open or close an inlet of the steam chamber; and an outlet door configured to open or close an outlet of the steam chamber, wherein each of the steam chamber upper member and the steam chamber lower member comprises a housing defining a steam cham-
(Continued)

ber inner space and a plurality of reinforcement ribs formed on a surface of the housing at a predetermined height.

14 Claims, 6 Drawing Sheets

(51) Int. Cl.
    *A23B 9/02*     (2006.01)
    *A23L 7/196*     (2016.01)
    *A23L 5/10*     (2016.01)
    *A23L 7/148*     (2016.01)
    *A23L 3/00*     (2006.01)
    *A23L 3/10*     (2006.01)

(52) U.S. Cl.
    CPC ............... *A23L 5/13* (2016.08); *A23L 7/148* (2016.08); *A23L 7/1965* (2016.08); *A61L 2/07* (2013.01); *A23L 3/003* (2013.01); *A61L 2202/121* (2013.01); *A61L 2202/23* (2013.01)

(56) References Cited

U.S. PATENT DOCUMENTS

| | | | | |
|---|---|---|---|---|
| 3,606,997 A | * | 9/1971 | Guckel | A23L 3/001 422/26 |
| 4,447,402 A | * | 5/1984 | Cox | B01J 3/04 219/404 |
| 4,728,504 A | * | 3/1988 | Nichols | A61L 2/26 206/366 |
| 6,241,117 B1 | * | 6/2001 | Wickins | B65D 88/10 220/646 |
| 2005/0226096 A1 | * | 10/2005 | Damhuis | A23L 3/10 366/234 |
| 2014/0050634 A1 | * | 2/2014 | Bacik | A61L 2/07 422/297 |

FOREIGN PATENT DOCUMENTS

| | | |
|---|---|---|
| JP | 2000-32966 A | 2/2000 |
| JP | 2000-106854 A | 4/2000 |
| JP | 2002-253186 A | 9/2002 |
| JP | 2008-133054 A | 6/2008 |
| KR | 10-0315993 B1 | 1/2002 |
| KR | 10-2008-0007191 A | 1/2008 |
| KR | 10-0874332 B1 | 12/2008 |
| KR | 10-2011-0032998 A | 3/2011 |
| KR | 10-1231997 B1 | 2/2013 |
| WO | 2011/037193 A1 | 3/2011 |

\* cited by examiner

Container input

FIG. 6

STERILIZER HAVING REINFORCEMENT RIB

BACKGROUND

Technical Field

The present disclosure relates to a sterilizer having a reinforcement rib, and more particularly to a sterilizer having a reinforcement rib, of which the durability, stability and productivity are improved due to the reinforcement.

Description of the Related Art

"Instant rice," which is rice obtained by cooking only white grains or white grain to which other grains are selectively added in a disposable container, is mass-produced and sold while being completely cooked. Thus, a consumer heats a product of instant rice at a constant temperature such that the consumer may easily eat the instant rice.

Figure 1:
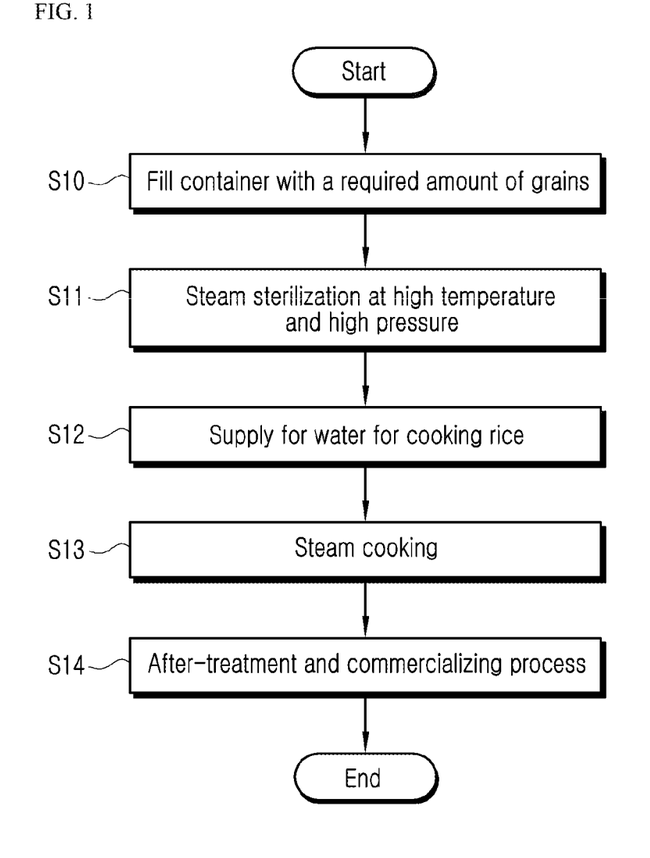
FIG. 1 is a flowchart illustrating a process of manufacturing instant rice.

A method of manufacturing instant rice will be described with reference to FIG. 1.

When a required amount of rice or other grain is filled in a disposable container in step S10, steam sterilization is performed in high-temperature high-pressure atmosphere in step S11. After supplying water for cooking rice in step S12, rice grain is steam-cooked in step S13. Various after-treatments such cover packaging and simmering of boiled rice and a commercializing process is performed in step S14 such that the instant rice is completed. In this case, the steam sterilizing step S11 is important for the purpose of food hygiene.

The present applicant has applied and used a sterilizer for performing the steam sterilization step for manufacturing instant rice (Korean Registered Patent No. 10-0874332).

However, when the sterilizer disclosed in the patent is used, the following problems have been found.

First, although the sterilization is performed at a temperature of 100~150° C. and a pressure of 3~3.5 $kg/cm^2$, when the sterilizer according to the related art is used, a welded portion cannot endure the steam pressure so that the welded portion is occasionally deformed. This may cause a safety or hygiene accident.

The deformation is caused in a part of a machine having a thin thickness and weakened due to the welding. To solve the problem, a thick component may be used, but, in this case, it is difficult to precisely manufacture or control a machine and the manufacturing cost is excessively increased.

Second, steam has been often leaked at an inlet or outlet through which a container is input or output.

In case of a sterilizer according to the related art, although a manner that a door is opened or closed by a rotary cylinder after the door horizontally moves by a reciprocating cylinder has been applied to enhance airtightness, when the door is opened or closed in such a manner, the durability of a connecting portion between the door and the machine main body has been deteriorated.

Third, various container cannot be used.

Thus, separated sterilizers and manufacturing lines are required for various sizes of containers, so that the productivity has been deteriorated.

RELATED ARTS

Korean Registered Patent No. 10-0874332
Korean Registered Patent No. 10-0315993
Korean Patent Publication No. 2011-0032998
International Publication No. WO 2011/037193

BRIEF SUMMARY

Technical Problem

The present disclosure is created to solve the problems described above.

In detail, the present disclosure is to provide a sterilizer which is capable of enduring the environment of high-temperature high-pressure environment of a steam chamber while the thickness of a portion of an inner wall of a steam chamber is not thinned due to a welding.

In particularly, the present disclosure is to provide a door which has durability sufficient to endure the high temperature and high pressure while the air-tightness is maintained.

In addition, the present disclosure is to provide a sterilizer capable of containing containers of various sizes.

Technical Solution

To solve the problems, in accordance with an aspect of the present disclosure, there is provided a sterilizer which includes: a steam chamber comprising a steam chamber upper member (201) and a steam chamber lower member (202) which are bolt-coupled to each other; an inlet door (110) configured to open or close an inlet (210) of the steam chamber; and an outlet door (120) configured to open or close an outlet (220) of the steam chamber, wherein each of the steam chamber upper member (201) and the steam chamber lower member (202) includes a housing (241, 242) defining a steam chamber inner space and a plurality of reinforcement ribs (251, 252) formed on a surface of the housing at a predetermined height.

Preferably, the sterilizer further includes flanges (281, 282) extending in a lateral direction and provided to a lower end of the housing (241) of the steam chamber upper member (201) and an upper end of the housing (242) of the steam chamber lower member (202), respectively, wherein a plurality of bolt coupling holes (271, 272) are formed on the flanges (281, 282) and housing bolts (270) pass through the coupling holes (271, 272) to be bolt-coupled such that the steam chamber upper member (201) and the steam chamber lower member (202) are coupled to each other.

Preferably, the inlet door (110) and the outlet door (120) includes door plates (111, 121) configured to open or close the inlet (210) and the outlet (220), and a plurality of door reinforcement ribs (112, 122) formed from the door plates (111, 121) toward an outside at a predetermined height, and a width of the door reinforcement ribs (112, 122) is wider than a width of the reinforcement ribs (251, 252).

Preferably, each of the inlet and outlet doors (110, 120) is provided with two door reinforcement ribs (112, 122) in a lateral direction about the door plate (111, 121), one side of each rotational member (113, 123) is rotatably connected to the door plate (111, 121) at a position facing the two door reinforcement ribs (112, 122), an opposite side of each rotational member (113, 123) is rotatably connected to a fixed rotation shaft connection part (114, 124), and the rotational members (113, 123) are rotated by hydraulic cylinders (150, 160) such that the inlet and outlet doors (110, 120) are opened or closed.

Preferably, a bottom surface (211) of an inner space of the steam chamber is inclined toward an outside, and the bottom surface (211) is concaved at a predetermined width to form a drain part (212).

Preferably, the sterilizer further includes a plurality of air supply and exhaust parts (300) communicating with the housing (241) of the steam chamber upper member (201), wherein the air supply and exhaust parts (300) are provided in plural paired rows, each of which includes an air supply part and an air exhaust part.

Preferably, each of the air supply and exhaust parts of the air supply and exhaust parts (300) includes: an inner second flange (370) coupled to the housing (241); an inner first flange (360) bolt-coupled to the inner second flange (370); a hose (340) having one side seal-connected to the inner first flange (360); an opening/closing valve (350) provided on the hose (340) to open or close the hose (340); an outer second flange (330) seal-connected to an opposite side of the hose (340); and an outer first flange (320) bolt-coupled to the outer second flange (330).

Preferably, the air supply and exhaust parts (300) includes five paired rows of which first, third and fifth rows are air exhaust parts and second and fourth rows are air supply parts, connecting holes (311A, 311B, 313A, 313B, 315A, 315B) provided on the outer first flange (320) of the air exhaust part of the air supply and exhaust part (300) are connected to an outer air exhaust apparatus, and connecting holes (312A, 312B, 314A, 314B) provided on the outer first flange (320) of the air supply part of the air supply and exhaust part (300) are connected to a steam supply apparatus.

Preferably, the sterilizer further includes a pressure reducing valve provided to the steam chamber to perform a pressure reducing function such that a pressure of the steam chamber is equal to a predetermined pressure.

Preferably, the sterilizer further includes a carrier (400) able to be introduced into the steam chamber through the inlet (210), and container inserting holes provided on the carrier (400) and having mutually different sizes.

Preferably, a container (1) which is inserted into the container inserting holes on the carrier (400) includes an instant rice container.

Advantageous Effects

According to the present disclosure, the thickness of the inner wall which is toward an outside based on the inner space of the steam chamber is constantly maintained and the plurality of reinforcement ribs are used to enhance the durability, so that it is possible to provide a safety-enhanced sterilizer.

The durability of the door is improved while maintaining the airtightness, and the closing or opening operation of the door is simple so that a sterilizer can be easily used.

In addition, containers having various sizes may be easily used in one sterilizer.

DETAILED DESCRIPTION

Hereinafter, an embodiment of the present disclosure will be described in detail with reference to the accompanying drawings.

Figure 2:
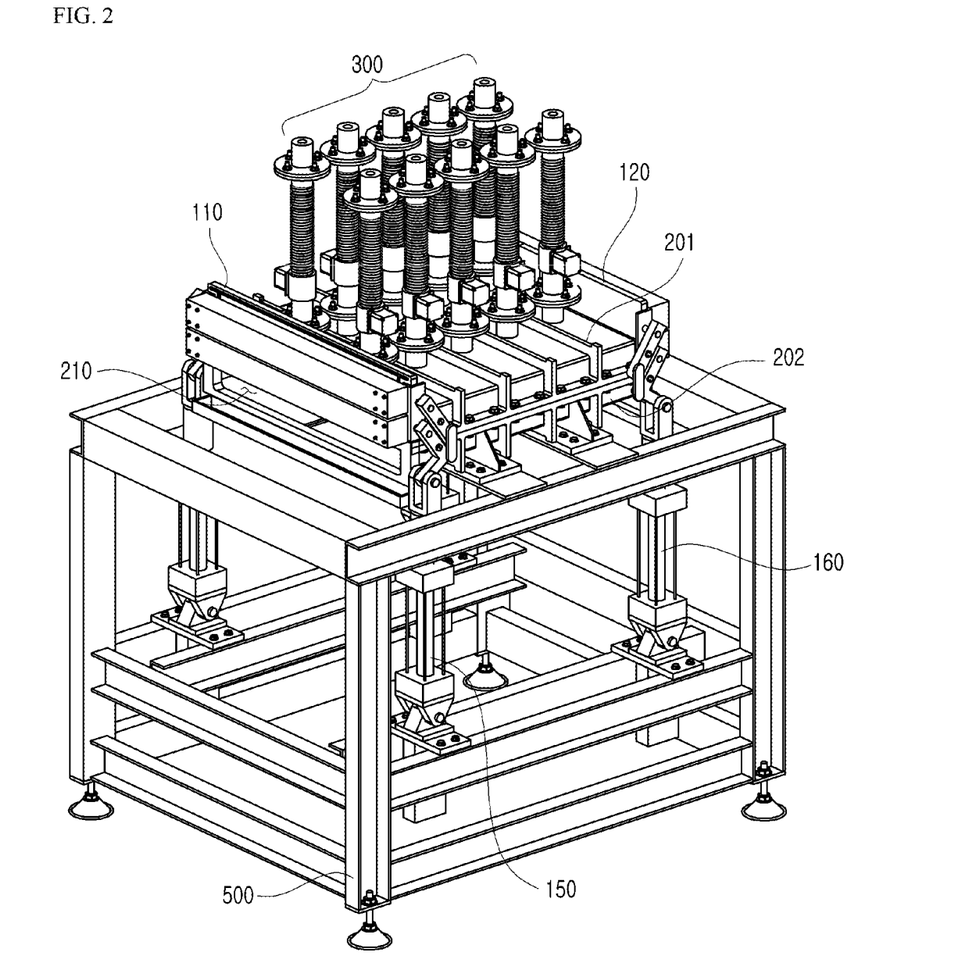
FIGS. 2 and 3 are perspective views illustrating a sterilizer according to the present disclosure.

A sterilizer according to the present disclosure will be described with reference to FIGS. 2 to 4.

A sterilizer according to the present disclosure substantially includes a door 110, 120, a steam chamber 201, 202, an air supply and exhaust part 300 and a support frame 500 for supporting the steam chamber.

Although not shown in the drawings, conveyor belts are sequentially connected to outsides of an inlet 210 and an outlet 220 of the steam chamber. A carrier 400 moves along the conveyor belts such that the carrier 400 is introduced into the sterilizer through the inlet 210. When a sterilizing process is completed the carrier 400 is again transferred through the outlet 220 along the conveyor belt for a next process.

First, the steam chamber will be described.

As described above, the steam chamber of the sterilizer is configured to have an inner wall which has a constant thickness from an inner space thereof toward an outside, such that the steam chamber is prevented from being deformed and steam is prevented from leaking.

To this end, the steam chamber, which has been manufactured through a welding scheme according to the related art, is manufactured through a bolt coupling scheme.

The steam chamber is divided into a steam chamber upper member 201 and a steam chamber lower member 202.

Each of the steam chamber upper and lower members 201, 202 includes a housing 241, 242, the inner wall of which defines the inner space of the steam chamber, a plurality of reinforcement ribs 251, 252 which is formed from an outer surface of the housing toward an outside at a predetermined height, and a flange 281, 282 which extends laterally from a lower or upper end of the housing 241, 242 of the upper or lower member.

The flanges 281, 282 are provided with bolt coupling holes 271, 272 for bolt coupling, such that the thickness of the inner wall from the inner space of the steam chamber toward an outside may be maintained to be constant through the bolt coupling. As well as the bolt coupling, a welding may be used.

In addition, the reinforcement ribs 251, 252 are configured to endure expansion force generated from the housing 241 or 242 toward an outside in a high-temperature and high-pressure environment of the inside of the steam chamber, so that high durability is provided. Similarly with the reinforcement ribs 251, 252, the flanges 281, 282 additionally provide lateral durability.

The bottom surface 211 of the inner space of the steam chamber is inclined such that the height is gradually lowered from the center toward the inlet 210 and the outlet 220. Thus, condensate water, which may be generated during a steam sterilization process, may be naturally exhausted to an outside. For the purpose of more natural exhaustion, a drain part 212 concaved in a predetermined width may be provided on the bottom surface 211 and a lower side end of the drain part 212 may communicate with an outside.

Next, the doors 110, 120 will be described.

An inlet door 110 for opening/closing the inlet 210 of the steam chamber is operatively connected to the inlet 210.

The inlet door 110 includes a door plate 111 which is an opened/closed part, and a plurality of door reinforcement ribs 112 which is provided laterally on the surface thereof and is formed toward an outside while having a predetermined height.

In this case, it is preferable that the width of the door reinforcement rib 112 is wider than that of the reinforcement rib 251, 252 provided on the inner wall of the steam chamber.

Preferably, two door reinforcement ribs 112 are provided. This improves the durability and is because of the connectivity with two rotational members 113 described below.

One side of the rotational member 113 is rotatably connected at a position on the door plate 111 corresponding to the two door reinforcement ribs 112. Since the weight of the reinforcement rib 112 is heavy, the door is more smoothly and precisely opened or closed as the rotational member 113 is rotated.

The opposite side of the rotational member 113 is rotatably connected to a fixed rotational shaft connection part 114. As a hydraulic cylinder 150 allows the rotational member 113 to be rotatable, the inlet door 110 is opened or closed.

Since the hydraulic cylinder 150 moving up or down is used instead of a reciprocating or rotary cylinder of a sterilizer according to the related art, a more precise motion is possible and the door may be certainly sealed such that any gaps through which steam is leaked do not exist.

The door plate 121, door reinforcement rib 122, rotational member 123, rotation shaft connection part 124 and hydraulic cylinder 160, which are used to open or close the outlet 220 and connected or provided to the outlet door 120, are the same as those of the inlet door 110.

Next, the air supply and exhaust part 300 will be described.

The plurality of air supply and exhaust parts 300 are installed on the housing 241 of the steam chamber upper member 201 to communicate with the housing 241.

The air supply and exhaust parts 300 include plural pairs of air supply parts and air exhaust parts which sequentially constitute plural rows by pairs.

Each of the air supply and exhaust parts 300 includes an inner second flange 370 coupled upward to an air supply and exhaust hole 231 of the housing 241, an inner first flange 360 bolt-coupled to the inner second flange 370, a hose 340 having one side seal-connected to the inner first flange 360, an opening/closing valve 350 provided on the hose 340 to open or close the hose 340, an outer second flange 330 seal-connected to the opposite side of the hose 340, and an outer first flange 320 bolt-coupled to the outer second flange 330. A connecting hole 310 is provided on the outer first flange 320.

Figure 5:
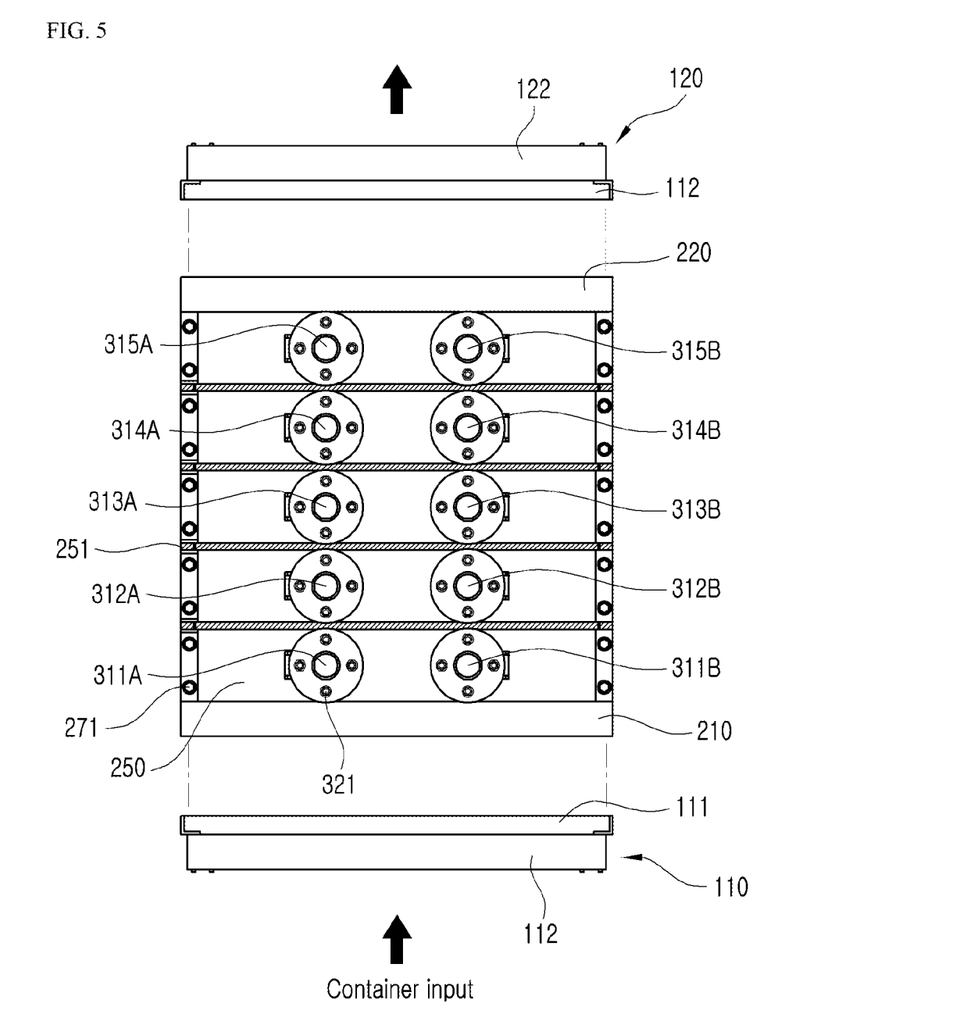
FIG. 5 is a plan view illustrating a steam chamber of a sterilizer according to the present disclosure, where an arrow represents a transporting direction of a container.

As shown in FIG. 5, according to an embodiment, the air supply and exhaust parts 300 include five paired rows of which the first, third and fifth rows are the air exhaust parts and the second and fourth rows are the air supply parts in the direction from the inlet 210 toward the outlet 220.

That is, connecting holes 311A, 311B, 313A, 313B, 315A, 315B provided on the outer first flange 320 of the air exhaust part are connected to an outer air exhaust apparatus (not shown), and connecting holes 312A, 312B, 314A, 314B provided on the outer first flange 320 of the air supply part are connected to a steam supply apparatus (not shown).

As described above, the air exhaust part and the air supply part alternate with each other, such that uniform air ventilation and uniform steam introduction may be performed in the inner space of the steam chamber. Thus, even though the plurality of containers 1 are widely introduced into the inner space of the steam chamber, the sterilization may be uniformly performed.

Meanwhile, a pressure meter (not shown) for measuring an inner pressure of the steam chamber and a pressure reducing valve (not shown) for performing a function of reducing the pressure to a predetermined pressure may be provided in the steam chamber. The pressure reducing valve (not shown) may be provided on the steam chamber lower member 202.

The carrier 400 is a member which goes into the steam chamber while being loaded with the containers 1.

Figure 3:
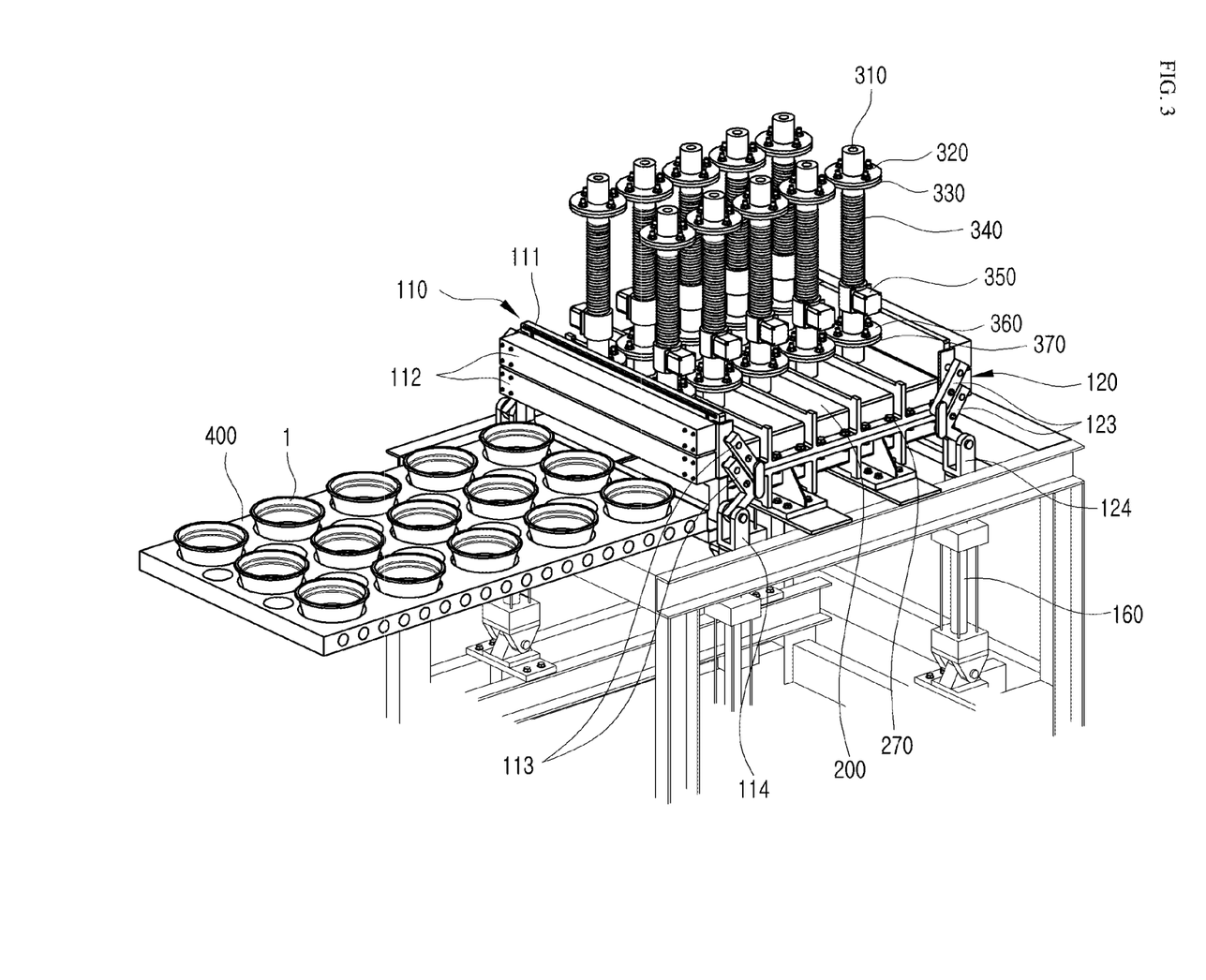
Figure 4:
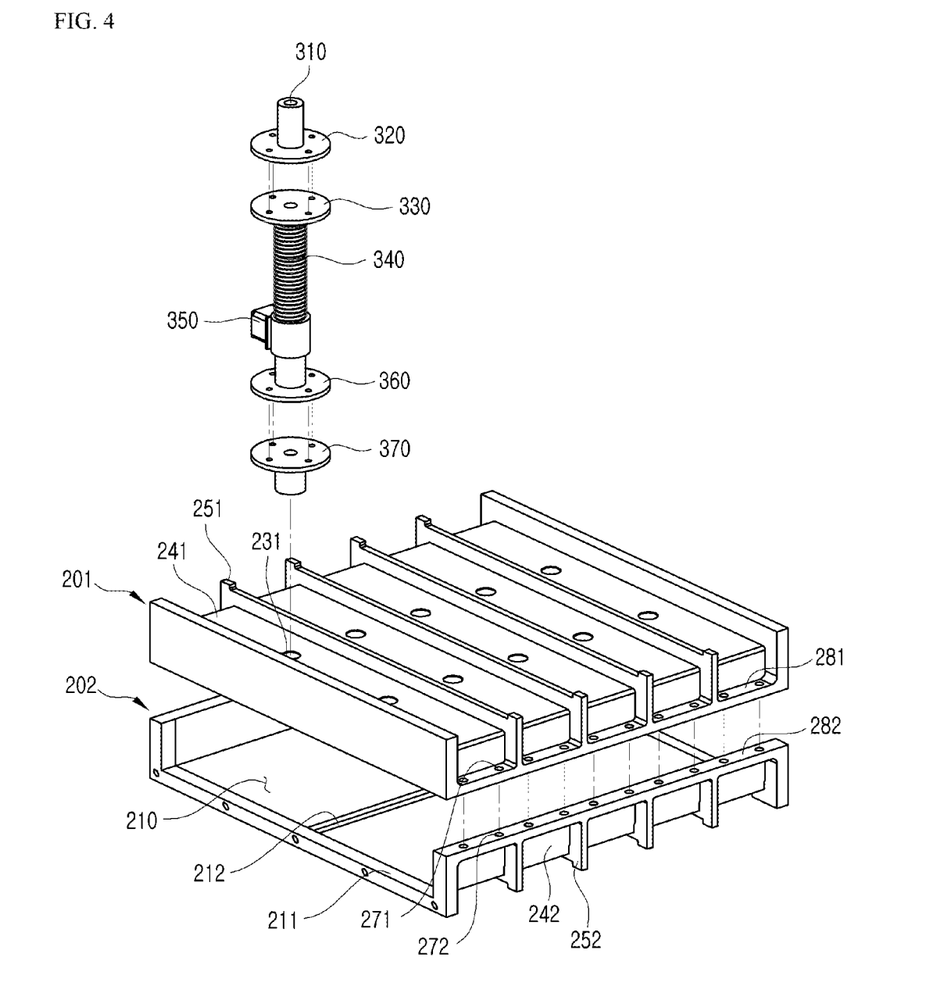
FIG. 4 is an exploded perspective view illustrating a steam chamber of a sterilizer according to the present disclosure.

As shown in FIG. 3, it is preferable to provide container inserting holes having mutually different sizes on the carrier 400. Thus, the same carriers 400 and the containers 1 having various sizes may be used.

In case of the carrier shown in FIG. 3, fifteen containers 1 may be sterilized at a time, and three types of containers 1 of 130 g, 210 g and 300 g may be selectively used.

Figure 6:
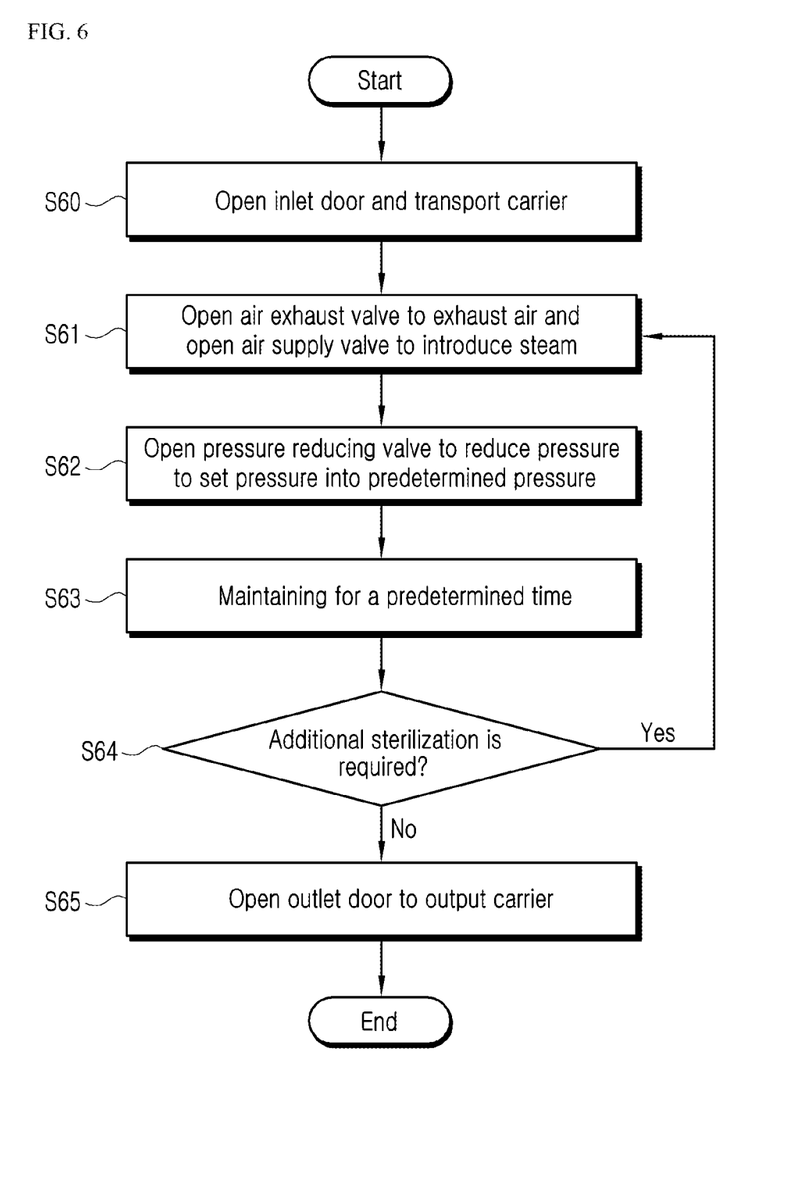
FIG. 6 is a flowchart illustrating a sterilizing process utilized by a sterilizer according to the present disclosure.

A sterilizing method using a sterilizer according to the present disclosure will be described with reference to FIG. 6.

First, in step S60, the inlet door 110 is opened and the container 1 filled with grains is introduced into the inner space of the steam chamber through the conveyer belt by using the carrier 400.

Next, in step S61, the opening/closing valve 350 of the air exhaust part is opened to exhaust residual air in the inner space of the steam chamber and at the same time, the opening/closing valve 350 of the air supply part is opened to introduce steam into the inner space of the steam chamber.

In step S62, in general, after steam is input at a desired pressure or more, the pressure of the inner space of the steam chamber is automatically adjusted in such a manner that the pressure reducing valve (not shown) is opened to reduce the pressure while confirming the pressure measured by the pressure meter (not shown).

Such a state is maintained for a predetermined time period in step S63.

When the container 1 is sterilized several times and is required to be additionally sterilized in step S64, the above-described procedure is repeated. When the sterilization is performed the predetermined number of times, in step S65, the outlet door 120 is opened to output the carrier 400 and the carrier 400 is transported through the conveyor belt for a next process.

Although the preferred embodiments of the present disclosure have been described, the present disclosure is not limited to the embodiments. That is, the present disclosure can be variously changed and modified by those skilled in the art without departing from the spirit and scope of the present disclosure, and all the changes and equivalents to the changes also fall within the scope of the present disclosure

DESCRIPTION OF REFERENCE NUMERALS

1: Container
110: Inlet door
120: Outlet door
111, 121: Door plate
112, 122: Door reinforcement rib
113, 123: Rotational member
114, 124: Rotational shaft connection part
150, 160: Hydraulic cylinder
201: Steam chamber upper member
202: Steam chamber lower member
210: Inlet 211: Steam chamber bottom surface
212: Drain part
231: Air supply and exhaust parts
241, 242: Housing
251, 252: Reinforcement rib
270: Housing connecting bolt
271, 272: Bolt coupling hole
281, 282: Flange
300: Air supply and exhaust part
310, 311A-315A, 311B-315B: Connecting hole
320: Outer first flange
330: Outer second flange
340: Connecting hose
350: Opening/closing valve
360: Inner first flange
370: Inner second flange
400: Carrier
500: Support frame The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sterilizer, comprising:
   a steam chamber comprising a steam chamber upper member and a steam chamber lower member which are bolt-coupled to each other;
   an inlet door configured to open or close an inlet of the steam chamber; and
   an outlet door configured to open or close an outlet of the steam chamber,
   wherein each of the steam chamber upper member and the steam chamber lower member comprises a housing defining a steam chamber inner space;
   wherein each of the steam chamber upper member and the steam chamber lower member comprises a plurality of housing reinforcement ribs, each of the ribs having a predetermined height;
   wherein the inlet door includes an inlet door plate configured to open or close the inlet and a plurality of inlet door reinforcement ribs formed from the inlet door plate toward an outside at a predetermined height, and widths of the inlet door reinforcement ribs are wider than widths of the housing reinforcement ribs;
   wherein the outlet door includes an outlet door plate configured to open or close the outlet and a plurality of outlet door reinforcement ribs formed from the outlet door plate toward an outside at a predetermined height, and widths of the outlet door reinforcement ribs are wider than widths of the housing reinforcement ribs, and
   wherein each of the inlet and outlet doors is provided with the respective door reinforcement ribs in a lateral direction about the door plate and at least one rotational member.

2. The sterilizer of claim 1, further comprising flanges extending in a lateral direction and provided to a lower end of the housing of the steam chamber upper member and an upper end of the housing of the steam chamber lower member, respectively,
   wherein a plurality of bolt coupling holes are formed on the flanges and housing connecting bolts pass through the coupling holes to be bolt-coupled such that the steam chamber upper member and the steam chamber lower member are coupled to each other.

3. The sterilizer of claim 1, wherein:
   one side of each rotational member is rotatably connected to the respective door plate at a position facing the two door reinforcement ribs,
   an opposite side of each rotational member is rotatably connected to a respective rotation shaft connection part, and
   the rotational members are rotated by hydraulic cylinders such that the inlet and outlet doors are opened or closed.

4. The sterilizer of claim 1, wherein a bottom surface of an inner space of the steam chamber is inclined toward an outside, and
   the bottom surface is concaved at a predetermined width to form a drain part.

5. The sterilizer of claim 1, further comprising a plurality of air supply and exhaust parts communicating with the housing of the steam chamber upper member,
   wherein the air supply and exhaust parts are provided in plural paired rows.

6. The sterilizer of claim 5, wherein each of the air supply part and the air exhaust part of the air supply and exhaust parts comprises:
   an inner second flange coupled to the housing;
   an inner first flange bolt-coupled to the inner second flange;
   a hose having one side seal-connected to the inner first flange;
   an opening/closing valve provided on the hose to open or close the hose;
   an outer second flange seal-connected to an opposite side of the hose; and
   an outer first flange bolt-coupled to the outer second flange.

7. The sterilizer of claim 6, wherein the air supply and exhaust parts comprises five paired rows of which first, third and fifth rows are air exhaust parts and second and fourth rows are air supply parts,
   connecting holes provided on the outer first flange of the air exhaust part of the air supply and exhaust part are connected to an outer air exhaust apparatus, and
   connecting holes provided on the outer first flange of the air supply part of the air supply and exhaust part are connected to a steam supply apparatus.

8. The sterilizer of claim 1, further comprising a pressure reducing valve provided to the steam chamber to perform a pressure reducing function such that a pressure of the steam chamber is equal to a predetermined pressure.

9. The sterilizer of claim 1, further comprising a carrier able to be introduced into the steam chamber through the inlet, and
   container inserting holes provided on the carrier and having mutually different sizes.

10. The sterilizer of claim 9, wherein a container which is inserted into the container inserting holes on the carrier includes an instant rice container.

11. The sterilizer of claim 1 wherein a bottom surface of the steam chamber inner space is inclined such that a height gradually lowers from a center toward the inlet of the steam chamber and from the center toward the outlet of the steam chamber.

12. A sterilizing method using a sterilizer, the method comprising:
   providing the sterilizer, the sterilizer including:
      a steam chamber comprising a steam chamber upper member and a steam chamber lower member which are bolt-coupled to each other;
      an inlet door configured to open or close an inlet of the steam chamber; and
      an outlet door configured to open or close an outlet of the steam chamber;
      wherein each of the steam chamber upper member and the steam chamber lower member comprises a housing defining a steam chamber inner space;
      wherein each of the steam chamber upper member and the steam chamber lower member comprises a plurality of housing reinforcement ribs, each of the ribs having a predetermined height;
      wherein the inlet door includes an inlet door plate configured to open or close the inlet and a plurality of inlet door reinforcement ribs formed from the inlet door plate toward an outside at a predetermined height; and widths of the inlet door reinforcement ribs are wider than widths of the housing reinforcement ribs;
      wherein the outlet door includes an outlet door plate configured to open or close the outlet and a plurality of outlet door reinforcement ribs formed from the outlet door plate toward an outside at a predetermined height; and widths of the outlet door reinforcement ribs are wider than widths of the housing reinforcement ribs; and
      wherein each of the inlet and outlet doors is provided with the respective door reinforcement ribs in a lateral direction about the door plate and at least one rotational member;
   introducing a container which is filled with contents into the steam chamber inner space;
   exhausting residual air in the inner space of the steam chamber by an air exhaust part and introducing steam into the inner space of the steam chamber from an air supply part;
   adjusting a pressure of the inner space of the steam chamber to a predetermined pressure;
   maintaining the pressure of the inner space of the steam chamber; and
   sterilizing the contents.

13. The sterilizing method of claim 12, wherein the contents are grains.

14. A method of manufacturing instant rice comprising performing the method of claim 12 wherein the contents are instant rice.

* * * * *